(12) United States Patent
Lipkowski

(10) Patent No.: US 9,169,288 B2
(45) Date of Patent: Oct. 27, 2015

(54) PEPTIDOMIMETICS AND THEIR APPLICATION

(71) Applicant: Instytut Medycyny Doswiadczalnej i Klinicznej im. Miroslawa Mossakowskiego Polskiej Akademii Nauk, Warszawa (PL)

(72) Inventor: Andrzej Lipkowski, Warszawa (PL)

(73) Assignee: Instytut Medycyny Doswiadczalnej i Klinicznej im. Miroslawa Mossakowskiego Polskiej Akademii Nauk, Warsaw (PL)

( * ) Notice: Subject to any disclaimer, the term of this patent is extended or adjusted under 35 U.S.C. 154(b) by 0 days.

(21) Appl. No.: 14/007,714

(22) PCT Filed: Dec. 28, 2012

(86) PCT No.: PCT/IB2012/057792
§ 371 (c)(1),
(2) Date: Apr. 7, 2014

(87) PCT Pub. No.: WO2014/102571
PCT Pub. Date: Jul. 3, 2014

(65) Prior Publication Data
US 2014/0303095 A1    Oct. 9, 2014

(51) Int. Cl.
*A61K 38/06* (2006.01)
*A61K 38/07* (2006.01)
*C07K 5/10* (2006.01)
*C07K 5/087* (2006.01)
*C07K 5/107* (2006.01)
*C07K 5/065* (2006.01)
*C07K 5/06* (2006.01)
*C07K 5/08* (2006.01)
*A61K 38/00* (2006.01)
*A61K 9/00* (2006.01)
*A61K 9/20* (2006.01)

(52) U.S. Cl.
CPC ... *C07K 5/10* (2013.01); *C07K 5/06* (2013.01); *C07K 5/06078* (2013.01); *C07K 5/08* (2013.01); *C07K 5/0812* (2013.01); *C07K 5/1016* (2013.01); *A61K 9/0019* (2013.01); *A61K 9/20* (2013.01); *A61K 38/00* (2013.01)

(58) Field of Classification Search
CPC .. A61K 31/495; A61K 31/4545; A61K 38/00
See application file for complete search history.

(56) References Cited

FOREIGN PATENT DOCUMENTS

WO       03031407 A2    4/2003
WO    2011035142 A1    3/2011

OTHER PUBLICATIONS

Amino-acid residue: EMBL-EBI, http://www.ebi.ac.uk/chebi/searchld.do?chebild=33708, accessed on Feb. 9, 2015.*
International Search Report issued in corresponding International Patent Application No. PCT/IB2012/057792 dated Mar. 19, 2013 (9 pages).

* cited by examiner

*Primary Examiner* — Marcela M Cordero Garcia
*Assistant Examiner* — Kaipeen Yang
(74) *Attorney, Agent, or Firm* — Kilyk & Bowersox, P.L.L.C.

(57) ABSTRACT

Novel peptidomimetics exhibiting affinity for opioid receptors, possessing a general formula shown in FIG. 1, for gastrointestinal or peripheral administration in the form of a pill, infusion, injection or implant in the treatment of peripheral opioids side effects, particularly constipation or/and respiratory depression.

3 Claims, 1 Drawing Sheet

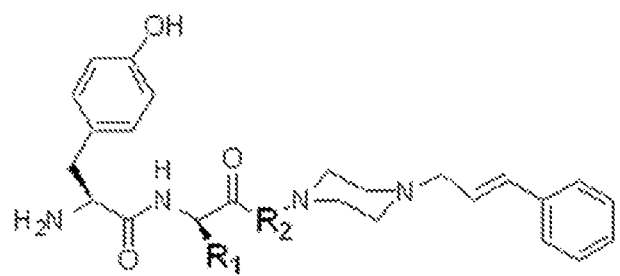

PEPTIDOMIMETICS AND THEIR APPLICATION

This application is a National Stage Application of PCT/IB2012/057792, filed Dec. 28, 2012.

BACKGROUND OF THE INVENTION (1) Field of the Invention

The subject of the present invention comprises novel peptidomimetics exhibiting affinity for opioid receptors, possessing the general formula shown in FIG. 1, for gastrointestinal or peripheral administration in the form of a pill, infusion, injection or implant in the treatment of peripheral opioids side effects, particularly constipation or/and respiratory depression.

(2) Description of Related Art

The applications of oral pills or transdermal patches with opiate drugs are the most common treatments of severe acute or chronic pain. These compounds non-specifically distributed over the whole body, beside analgesic effects in the central nervous system, which produce side effects (respiratory depression, constipation, tolerance, sedation, etc.) to such extent that pain treatment is reduced by doctors or refused by the patients. Especially, constipation is the most harmful side effect. The incidence of opioid-induced constipation in patients with non-malignant pain is about 40% [Camilleri M. American Journal of Gastroenterology 2011; 106 (5):835-842]. In one study, a third of patients receiving opioid therapy for chronic pain missed or decreased doses or stopped medication due to constipation [Bell T J, Panchal S J, et al. Pain Medicine 2009; 10(1):35-42].

The available therapies for opioid-induced constipation include oral laxatives, suppositories and the opioid antagonists, naloxone and methylnaltrexone. Because, non-specific laxatives only partially can be effective for opioid-induced constipation, recent developments have focused on medications which specifically target the mu receptor in the gut wall. Two therapies that are currently available are oral naloxone and parenteral methylnaltrexone [McNicol E, Boyce D B, et al. Pain Medicine 2008; 9 (6):634-659].

Naloxone is a competitive antagonist of opioid receptors. Orally, it actively reverses opioid agonist binding at the gut mu receptors. Naloxone undergoes extensive first-pass hepatic metabolism that results in reduction its systemic concentration. Unfortunately, this concentration is not predictable, especially in chronic ill patients often having hepatic problems.

Recently, subcutaneous methylnaltrexone has been proposed for the treatment of opioid-induced constipation as a peripherally acting opioid antagonist with restricted ability to cross the blond-brain barrier. [Thomas J, Karver S, et al. New England Journal of Medicine 2008; 358 (22):2332-2343]. Although, methylnaltrexone is quite specifically acting in healthy volunteers, its antagonist against opioid analgesia in chronically ill patients has to be taken into consideration.

BRIEF SUMMARY OF THE INVENTION

The subject of the present invention are compounds with the general formula (shown in FIG. 1):

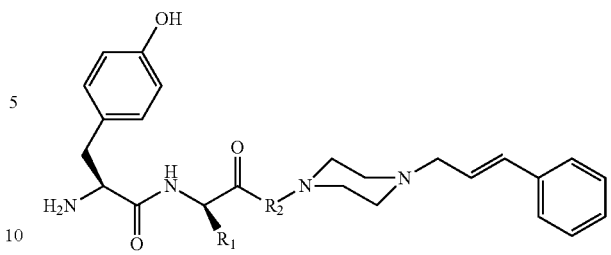

where: $R_1$ denotes a side chain of a D-amino acid selected from among: D-alanine, D-threonine, D-serine, D-methionine, D-leucine, D-glutamine, D-asparagine, D-arginine, D-lysine; $R_2$ denotes nothing or residue of glycine or dipeptide selected from among Gly-Phe, Gly-Trp.

In particular, the subject of the present invention are compounds selected from the group consisting of: Tyrosyl-D-alanyl-glycyl-cinnamylpiperazine, Tyrosyl-D-threonyl-glycyl-phenylalanyl-cinnamylpiperazine, Tyrosyl-D-arginyl-cinnamylpiperazine, and Tyrosyl-D-threonyl-cinnamylpiperazine.

Next aspect of the invention is a use of the peptide according to the invention, as defined above, in the production of an antagonist of opioid drugs.

BRIEF DESCRIPTION OF THE VIEW OF THE DRAWING

FIG. 1 shows a general formula of compounds of the present invention.

DETAILED DESCRIPTION

The drug produced can be designed for oral or peripheral administration to reverse constipation induced by opioid drugs. Particularly, the drug produced is designed to interact with opioid receptors. The drug produced can be in the form of oral pills for direct administration into gastrointestinal tract, or venous infusions for peripheral administration. Particularly, the drug produced is in the form of a multi-drug composition, especially containing opioid agonists used in pain therapy. The drug produced can be in the form of a composition containing a solid polymer that is the carrier for the active substances.

During structure-activity research of novel opioid peptidomimetics, it was unexpectedly shown that opioid peptide analogues that are hybridized with trans-1-cinnamylpiperazine with general formula presented on FIG. 1 expressed high affinity to opioid receptors, particularly mu opioid receptors, but with antagonist activity to opioid medicines like morphine, fentanyl or opioid peptides like enkephalin or biphalin. In addition, it has been found that the peptidomimetics applied intravenously or orally in experimental animal pain model do not reduced antinociceptive central effects of co-applied opioid agonist like morphine or biphalin. However, peptidomimetics with opioid agonists applied intravenously or intraperitoneally reduced constipation induced by peripherally applied opioids. In addition, oral pre-application or co-application of peptidomimetics (with general formula on FIG. 1) with opioid like morphine or loperamide strongly reversed constipation symptoms induced by opioid.

To better illustrate the activity of the present invention consisting of the anticonstipation activity resulted by opioid drugs use for analgesia, the following examples demonstrate the effectiveness of the compounds in animal models. However, the scope of the present invention should in no way be limited to the content of the examples below.

Example 1

Trans-1-Cinnamyl piperazine has been acylated with t-Boc-Tyr-D-Ala-Gly using N,N-dicyclohexylcarbodiimide with N-hydroxysucciimede coupling method in N,N'-dimethylformamide solution. After filtration of the N,N'-dicyclohexylurea, the crude intermediate product has been precipitated with water. Solid has been washed three times with water and dried. T-Butyloxycarbonyl protecting group has been removed with 5% hydrochloride in ethyl acetate. Final crude product as hydrochloride salt has been precipitated with ethyl ether. The crude product has been purified using HPLC preparative method in 0.5% hydrochloric acid/ethanol gradient system.

The pure product tyrosyl-D-alanyl-glycyl-cinnamylpiperazine hydrochloride (named peptidomimetic 1) has been used tested in mouse model of constipation induced by loperamide. The mice were divided into three groups one as control and two administered with loperamide hydrochloride (5 mg/kg). One group with loperamide, has been orally applied with peptidomimetic 1 (10 mg/kg), 30 minutes before loperamide, The wet weights of stools from each mouse were measured at 4 hours. It has been found that administration of loperamide induced constipation and in consequence, reduced stools over ten times, from 200 mg of control group to 15 mg of leperamide group. The pretreatment with peptidomimetic 1 significantly reversed loperamide effect resulted in 160 mg of stools (80%).

Example 2

Trans-1-Cinnamyl piperazine has been acylated with t-Boc-Tyr-D-Thr-Gly-Phe using N,N-dicyclohexylcarbodiimide with N-hydroxysucciimede coupling method in N,N'-dimethylformamide solution. After filtration of the N,N'-dicyclohexylurea, the crude intermediate product has been precipitated with water. Solid has been washed three times with water and dried. T-Butyloxycarbonyl protecting group has been removed with 5% hydrochloride in ethyl acetate. Final crude product as hydrochloride salt has been precipitated with ethyl ether. The crude product has been purified using HPLC preparative method in 0.5% hydrochloric acid/ethanol gradient system.

The pure product tyrosyl-D-threonyl-glycyl-phenylalanyl-cinnamylpiperazine hydrochloride (named peptidomimetic 2) has been used tested in mouse model of constipation induced by morphine. The mice were divided into three groups one as control and two administered intraperitoneally with morphine hydrochloride (5 mg/kg). One group with morphine, has been orally applied with peptidomimetic 2, 30 minutes before morphine, the wet weights of stools from each mouse were measured at 4 hours. It has been found that intraperitoneal administration of morphine induced constipation and in consequence, reduced stools near eight times, from 200 mg of control group to 25 mg of morphine group. The pretreatment with peptidomimetic 2 fully reversed morphine effect.

Example 3

Trans-1-Cinnamyl piperazine has been acylated with t-Boc-Tyr-D-Arg using N,N-dicyclohexylcarbodiimide with N-hydroxysucciimede coupling method in N,N'-dimethylformamide solution. After filtration of the N,N'-dicyclohexylurea, the crude intermediate product has been precipitated with water. Solid has been washed three times with water and dried. t-Butyloxycarbonyl protecting group has been removed with 5% hydrochloride in acetic acid. Final crude product as hydrochloride salt has been precipitated with ethyl ether. The crude product has been purified using HPLC preparative method in 0.5% hydrochloric acid/ethanol gradient system.

The pure product Tyrosyl-D-arginyl-cinnamylpiperazine dihydrochloride (named peptidomimetic 3) has been used tested in mouse model of constipation induced by loperamide. The mice were divided into three groups. The first group, defined as a control has been administered orally with soft depositions of 20% gum arabic at a volume of 0.1 ml/10 g body. The second group has been administered orally with soft depositions of 20% gum arabic containing equivalent of 5 mg/kg body of loperamide at a volume of 0.1 ml/10 g body. The third group has been administered orally with soft depositions of 20% gum arabic containing identical amount of loperamide and equivalent of 10 mg/kg body of peptidomimetic 3 at a volume of 0.1 ml/10 g body administered intraperitoneally The wet weights of stools from each mouse were measured at 4 hours. It has been found that oral administration of gum arabic containing loperamide induced constipation and in consequence, reduced stools near ten times, from 200 mg of control group to 22 mg of loperamide group. The application of peptidomimetic 3 with loperamide significantly reversed loperamide effect to 120 mg of stools (60%)

The invention claimed is:

1. Compound with the general formula:

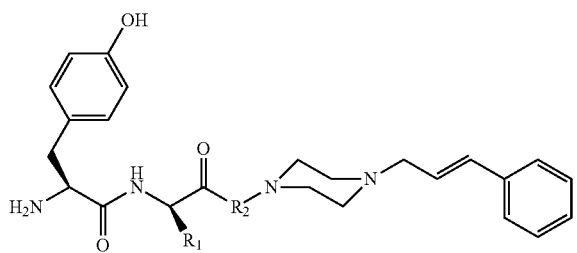

where:
- $R_1$ is a side chain of an amino acid where the amino acid is selected from D-alanine, D-threonine, D-serine, D-methionine, D-leucine, D-glutamine, D-asparagine, D-arginine, and D-lysine;
- $R_2$ denotes nothing or residue of glycine or dipeptide selected from among Gly-Phe, Gly-Trp.

2. Compound according to claim 1 selected from the group consisting of:
Tyrosyl-D-alanyl-glycyl-cinnamylpiperazine,
Tyrosyl-D-threonyl-glycyl-phenylalanyl-cinnamylpiperazine,
Tyrosyl-D-arginyl-cinnamylpiperazine, and Tyrosyl-D-threonyl-cinnamylpiperazine.

3. Compound according to claim 1, wherein $R_1$ is a side chain of an amino acid selected from D-alanine, D-threonine, and D-arginine.

* * * * *